United States Patent [19]
Schlapfer et al.

[11] Patent Number: 5,616,143
[45] Date of Patent: Apr. 1, 1997

[54] SURGICAL FORCEPS

[76] Inventors: Johannes F. Schlapfer, Leimen, CH-8750 Glarus; Martin Hess, Schutzenstrasse 2, CH-4434 Holstein, both of Switzerland

[21] Appl. No.: 383,877

[22] Filed: Feb. 6, 1995

[51] Int. Cl.$^6$ .................................................. A61B 17/56
[52] U.S. Cl. .............................. 606/61; 606/60; 606/205
[58] Field of Search ................................ 606/205, 206, 606/207, 208, 61, 60, 90, 105

[56] References Cited

U.S. PATENT DOCUMENTS

| | | | |
|---|---|---|---|
| 4,898,161 | 2/1990 | Grundei | 606/90 X |
| 5,364,397 | 11/1994 | Hayes et al. | 606/61 |
| 5,368,596 | 11/1994 | Burkhart | 606/208 X |

Primary Examiner—Michael Powell Buiz
Assistant Examiner—Kevin Truong

[57] ABSTRACT

Surgical forceps have connecting members onto which working ends are attached in offset fashion, so that they can work together outside the plane of the forceps. One of the working ends is tubular and the other has an angled, U-shaped cross section which receives a portion of the tubular working end. With the tubular working end slipped over a pedicle screw attached to a vertebrae and the other end attached to a support rod, the vertebra can be brought to the support simply and expeditiously.

5 Claims, 2 Drawing Sheets

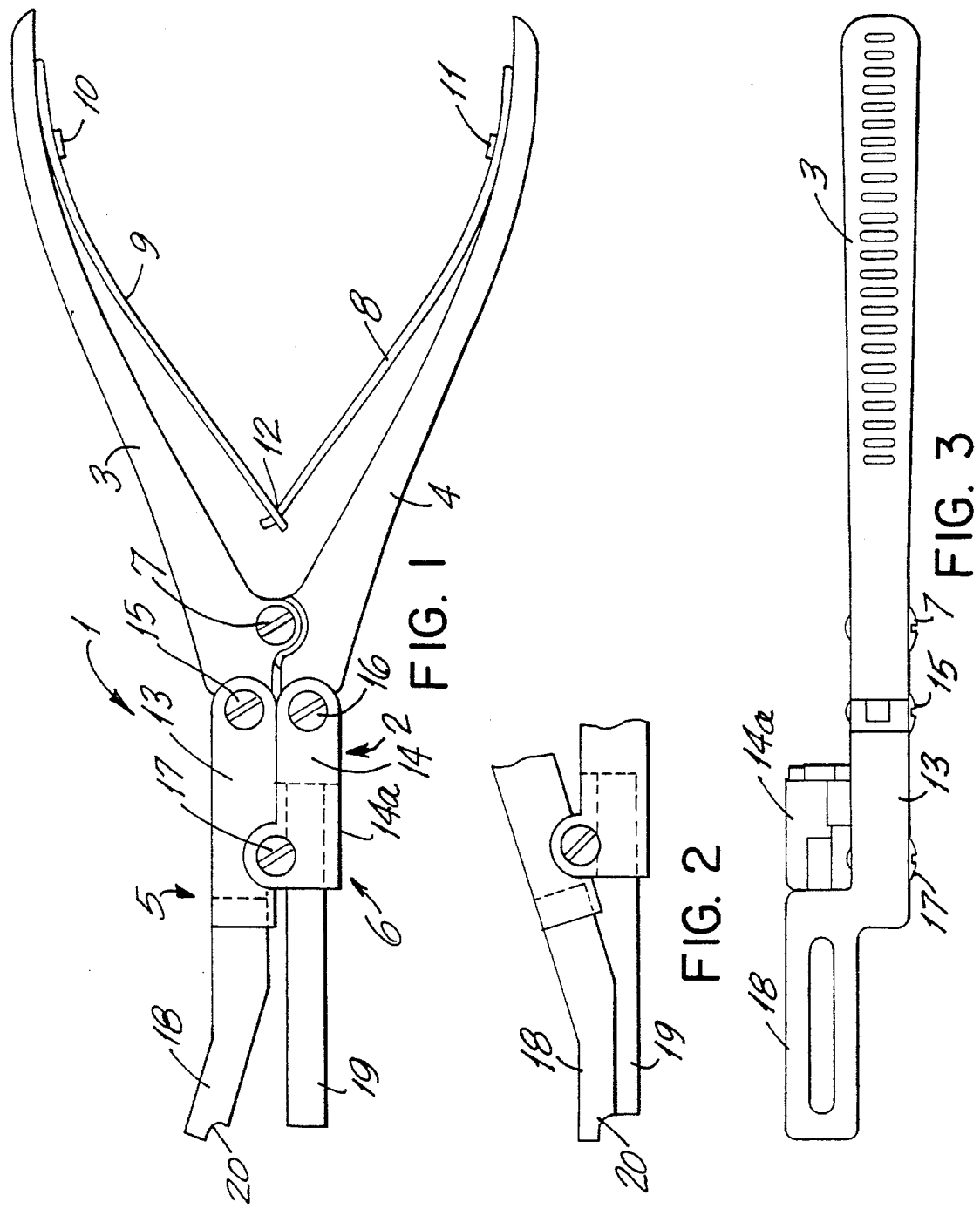

SURGICAL FORCEPS

FIELD OF THE INVENTION

The present invention relates to surgical forceps for use in spinal column surgery.

BACKGROUND OF THE INVENTION

For the correction of lateral and rotational spinal column deformations, two healthy spinal column fixation points at the ends of the affected area are chosen, into which spinal column implants such as pedicle screws are inserted. The implants are bridged by a support rod. At least one of the dislocated vertebrae between the two basic implants is also equipped with an implant such as a pedicle screw. To accomplish the desired correction, the dislocated vertebrae with implant in place must be brought to the support rod and fixed to the rod in the correct position. It often happens that the correction process causes not only a lateral displacement of the implants but also a pulling up of the implant.

The surgical forceps of the invention is designed to bring the dislocated, instrument-treated vertebrae to the support rod, and fasten the implants in the dislocated vertebrae to the support rod. The object of the present invention, then, is to provide a tool to position the implants attached to the dislocated vertebrae simply, safely and quickly on the support rod.

SUMMARY OF THE INVENTION

In accordance with the invention, there is provided a surgical forceps for positioning spinal column implants relative to a support rod comprising two operational elements, each comprising a handgrip and an operating end, pivot means connecting said operational elements to close said operating ends most remote from said handgrips when said handgrips are closed, one of said operating ends comprising means for attachment to a support rod and the other comprising means for connection to an implant whereby when said handgrips are closed an implant can be moved to a position on a support rod.

The operational elements in the forceps according to the invention have working ends joined at an angle with connecting members, so that they work together outside the forceps plane. To do this they are configured in such a way that in the closed position they grip in interlocking fashion. One of the working ends has a part with a U-shaped cross section, shaped concavely on the inner side, i.e. the side toward the other working end, and on the outside has three flat surfaces. The other working end is shaped as a continuous tube, so that when the forceps are closed, the tube portion rests in the concave part. In this way a screw shank linked to the implant seated in a vertebra, can be slid up onto the tube section of one working end while the U-shaped part of the other working end can be engaged with the support rod. By this means, outstanding manipulating capability can be achieved.

BRIEF DESCRIPTION OF THE DRAWINGS

The invention will be further described with reference to the accompanying drawings in which:

FIG. 1 is a side elevational view of a surgical forceps according to the invention in the open position;

FIG. 2 is a fragmentary view in side elevation of the surgical forceps of FIG. 1 in a closed position;

FIG. 3 is a plan view of the forceps of FIGS. 1 and 2; and

DETAILED DESCRIPTION OF THE INVENTION

Figure 4:
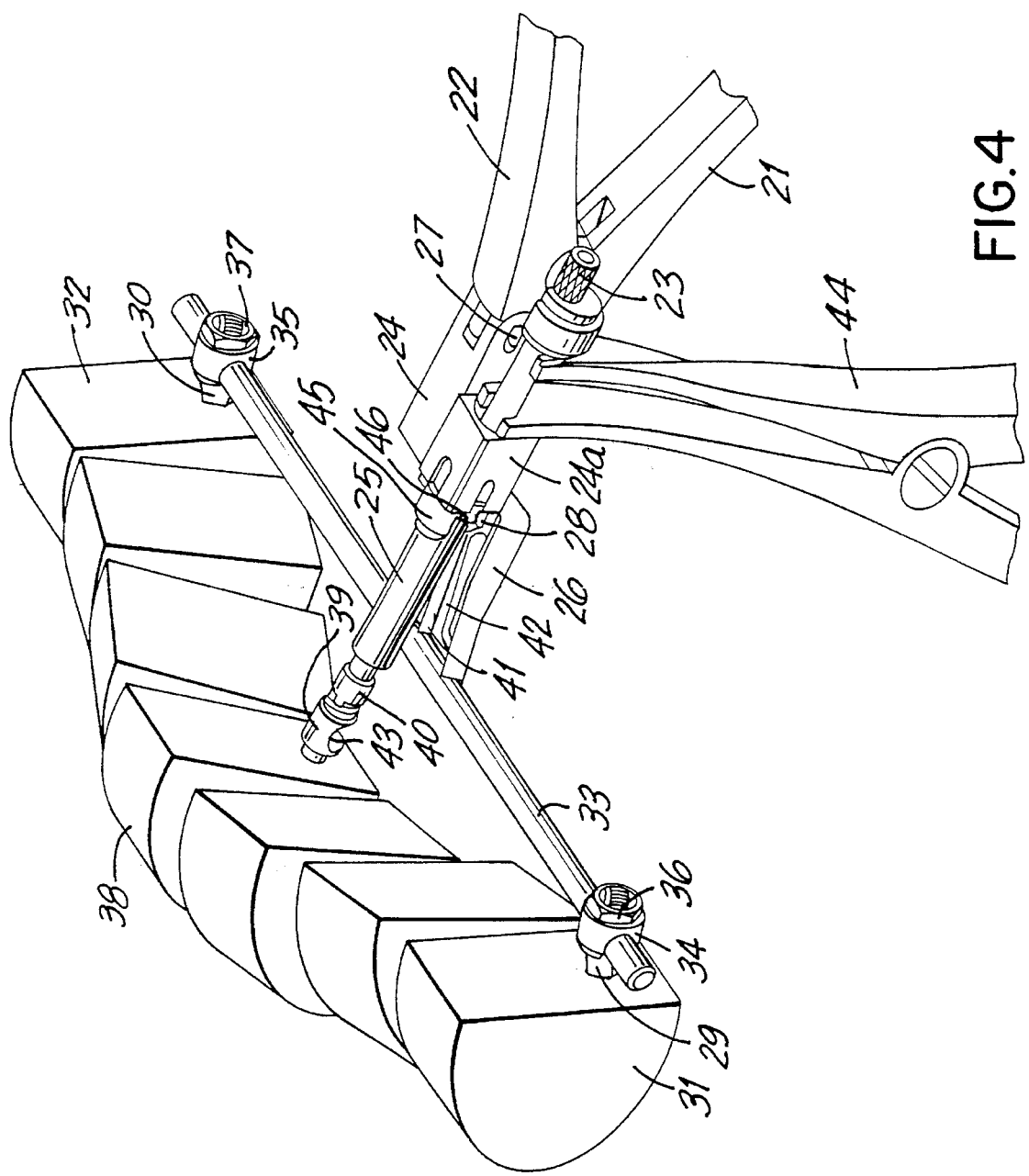
FIG. 4 is a perspective view showing the use of a forceps according to the invention during a spinal column operation.

Referring to FIG. 1, forceps according to the invention comprise two operational elements indicated generally and 1 and 2. Each operational element includes a handgrip (3, 4) and an operating end (5, 6). The handgrips 3 and 4 are pivotally connected at their ends adjacent the operating ends by a hinge 7. The handgrips are forced apart by two leaf springs 8 and 9 attached to the inner sides of the handgrips by screws 10 and 11. The leaf springs are themselves attached at 12 by simple mechanical forked engagement or may be more firmly connected, for example by welding, as desired.

The handgrips 3 and 4 are themselves attached to two connecting members 13 and 14 (parts of operating ends 5 and 6) via hinges 15 and 16. The connecting members are themselves pivotally connected by a hinge 17. The linkage is such that, as shown in FIG. 1, when the forceps are in their "at rest" position with the handgrips forced apart by springs 8, 9, the connecting members 13 and 14 lie parallel to one another.

Each of the connecting members 13 and 14 has attached to it a working end (18, 19). Each connecting member is partly offset (as shown in FIG. 3) so that the working ends 18, 19 are in different plane from the plane (FIG. 3) of the rest of the forceps. Connecting member 14 comprises a section 14a having the shape of a parallelopiped head. Into the section 14a, a working end 19, tubular in shape, is fitted. The tubular working end 19 is shaped so that a positioning socket can be slid over it. Working end 18 is angled outwardly as shown in FIG. 1. It has a U-shaped cross section with a concave interior facing the working end 19. As shown in FIG. 2, when the handgrips are brought together against the action of the springs 8 and 9, connecting members 13 and 14 rock on hinge 17 causing the working ends 18 and 19 to meet with the U-shaped channel of end 18 fitting over the cylinder or tube of end 19.

At its tip, the working end 18 has an arcuate cut out 20 on its two sides. This accommodates a support rod as will be explained below.

As explained above, when the handgrips 3 and 4 are closed, connecting members 13 and 14 move away from each other and working ends 18 and 19 come together. In an alternative construction (not shown) connecting member 13 may be rigidly connected to handgrip 3, with the elimination of hinge 15. In such a structure only connecting member 14 moves away from connecting member 13 and thus only working end 19 moves toward working end 18.

Operation of a forceps according to the invention will now be described in connection with FIG. 4 which shows a somewhat modified form of the device. Again, the forceps according to the invention comprises two handgrips 21 and 22, pivotally attached to each other at 23. Spring means (not shown), similar to the leaf springs 8, 9 of FIGS. 1, keeps the handgrips apart. The handgrips are pivotally attached to connecting members, only one of which, 24, appears in FIG. 4. Connecting member 24 has an offset portion 24a in the shape of a parallelopiped in which is seated a tubular working end 25. In FIG. 4, working end 26 of the other connecting member appears below working end 25. The connecting members are pivotally attached to the handgrips as at 27 and to each other as at 28.

In use, as shown in FIG. 4, two pedicle screws 29, 30 are anchored in two healthy vertebrae 31, 32. These screws are of the type having a side channel or socket in its head and a threaded stud at the top of the head. A support rod 33 is fitted into the side socket 43 of screws 29, 30 and clamped by the use of positioning sleeves 34, 35 and nuts 36, 37 which are turned down on the threaded studs.

The spinal segment illustrated schematically in FIG. 4 has displaced or defective vertebrae such as 38. A pedicle screw 39 of the same type as screws 29 and 30 is driven into vertebra 38 using a screw extension 40. When screw 39 has been anchored, the tubular offset working end 25 attached to the connecting member 24 is slid over the screw extension 40 which is still connected to the screw 39. The interior of the tubular end 25 is dimensioned for this purpose. The other working end 26 of the forceps is then applied to the support rod 33, with its arcuate cut out 41 engaging the rod. When the forceps are manipulated by closing the handgrips 21, 22, tubular member 25 moves into the concave recess 42 of working end 26. With this, defective vertebra 38 is brought towards the support rod 33.

To bring up screw 39 with its side socket 43 to support rod 33, a conventional forceps 44 is used to lift screw extension 40 allowing it to go securely into tube 25.

Prior to engaging the forceps according to the invention, a positioning sleeve 45 had been slid onto tube 25, being retained there by a leaf spring 46 mounted on the inside of offset part 24a of connecting member 24. With the pedicle screw 39 secured on support rod 33, positioning sleeve 45 is loosened and gravity causes it to drop onto the support rod and the pedicle screw. If the recess of the socket is not immediately fitted to the support rod, the surgeon will move it to the proper position. Thereafter, the forceps of the invention is no longer needed and the screw 39 is secured by a nut such as 36 or 37.

If more than one defective vertebra must be corrected, they are brought up to the support rod between the two healthy vertebrae in the manner just described, and secured in place. With the aid of the surgical forceps according to the invention, a dislocated vertebra can be moved smoothly and exactly to a correcting position, lifted easily and quickly, positioned on the support rod and fixed, using a positioning sleeve 26 such as those described, which converts the open implant into a closed implant. Time spent doing the surgery is shortened significantly.

What is claimed is:

1. Surgical forceps for positioning spinal column implants relative to a support rod comprising two operational elements, each comprising a handgrip and an operating end, pivot means connecting said operational elements to close said operating ends when said handgrips are closed, one of said operating ends comprising means for attachment to a support rod and the other operating end comprises means for connection to an implant whereby when said handgrips are being closed, an implant can be moved to a position on a support rod.

2. The forceps claimed in claim 1 and comprising a first hinge means joining said handgrips at a point adjacent said operating ends, and spring means tending to force said handgrips apart, said operating ends each comprising a connecting member and a working end, second hinge means connecting each connecting member with its adjacent handgrip so that when said handgrips are forced apart by said spring, said connecting members will be parallel to each other, third hinge means joining said connecting members to one another adjacent said working ends, each of said working ends being offset from its associated connecting member, in the same direction.

3. Surgical forceps for positioning spinal column implants relative to a support rod comprising two operational elements each comprising a handgrip and an operating end, spring means tending to force said handgrips apart, said operating ends each comprising a connecting member and a working end, pivot means connecting said operational elements to close said operating ends when said handgrips are closed, said pivot means comprising first hinge means joining said handgrips at a point adjacent said operating ends, second hinge means connecting each connecting member with its adjacent handgrip so chat when said handgrips are forced apart by said spring, said connecting members will be parallel to each other, third hinge means joining said connecting members to one another adjacent said working ends, each of said working ends being offset from its associated connecting member in the same direction, the working end of one of said operating ends having a U-shaped cross section forming a concavity in the direction of the other working end and means for attachment to a support rod, the working end of the other operating end being tubular and dimensioned to fit over an extension on a spinal column implant and to seat in said concavity, whereby when said handgrips are closed, an implant can be moved to a position on a support rod.

4. The surgical forceps of claim 3, wherein said other working end comprises an element of parallelopiped shape offset from its associated connecting means and containing a tubular member, said parallelopiped shaped element having a leaf spring for holding a positioning socket on said tubular member.

5. The forceps of claim 3, wherein the working end having a U-shaped cross section has a round cut out on its tip to receive a round support rod.

\* \* \* \* \*

UNITED STATES PATENT AND TRADEMARK OFFICE
CERTIFICATE OF CORRECTION

PATENT NO. : 5,616,143
DATED : April 1, 1997
INVENTOR(S) : Johannes F. Schlapfer & Martin Hess It is certified that error appears in the above-identified patent and that said Letters Patent is hereby corrected as shown below:

Col. 4, (claim 1) line 5, delete "being".

Col. 4, (claim 3) line 29, "chat" should be --that--.

Signed and Sealed this

Tenth Day of March, 1998

Attest:

BRUCE LEHMAN

Attesting Officer

Commissioner of Patents and Trademarks